(12) United States Patent
Adeli-Mosabbeb et al.

(10) Patent No.: US 11,918,370 B2
(45) Date of Patent: Mar. 5, 2024

(54) SYSTEMS AND METHODS FOR ESTIMATION OF PARKINSON'S DISEASE GAIT IMPAIRMENT SEVERITY FROM VIDEOS USING MDS-UPDRS

(71) Applicant: The Board of Trustees of the Leland Stanford Junior University, Stanford, CA (US)

(72) Inventors: Ehsan Adeli-Mosabbeb, Stanford, CA (US); Mandy Lu, Mountain View, CA (US); Kathleen Poston, Stanford, CA (US); Juan Carlos Niebles, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 198 days.

(21) Appl. No.: 17/324,979

(22) Filed: May 19, 2021

(65) Prior Publication Data
US 2021/0386359 A1 Dec. 16, 2021

Related U.S. Application Data

(60) Provisional application No. 63/037,526, filed on Jun. 10, 2020.

(51) Int. Cl.
*G06T 7/20* (2017.01)
*A61B 5/00* (2006.01)
(Continued)

(52) U.S. Cl.
CPC .......... *A61B 5/4082* (2013.01); *A61B 5/1101* (2013.01); *A61B 5/1121* (2013.01);
(Continued)

(58) Field of Classification Search
CPC ... A61B 5/4082; A61B 5/1101; A61B 5/1121; A61B 5/1124; A61B 5/1128;
(Continued)

(56) References Cited

U.S. PATENT DOCUMENTS 11,288,802 B2 * 3/2022 Lo .................. G06T 7/0014
2007/0229522 A1 * 10/2007 Wang .................. A61B 5/1113
345/547
(Continued)

FOREIGN PATENT DOCUMENTS

WO WO-2017081609 A1 * 5/2017 .......... A61K 31/426
WO WO-2018236936 A1 * 12/2018 ............ A61B 34/10

OTHER PUBLICATIONS

Adeli et al., "Joint feature-sample selection and robust diagnosis of Parkinson's disease from MRI data", Neuroimage, Nov. 1, 2016, vol. 141, pp. 206-219, electronic publication Jun. 10, 2016, doi: 10.1016/j.neuroimage.2016.05.054.
(Continued)

*Primary Examiner* — Shefali D Goradia
(74) *Attorney, Agent, or Firm* — KPPB LLP (57) ABSTRACT

Many embodiments of the invention include systems and methods for evaluating motion from a video, the method includes identifying a target individual in a set of one or more frames in a video, analyzing the set of frames to determine a set of pose parameters, generating a 3D body mesh based on the pose parameters, identifying joint positions for the target individual in the set of frames based on the generated 3D body mesh, predicting a motion evaluation score based on the identified join positions, providing an output based on the motion evaluation score.

20 Claims, 7 Drawing Sheets

(51) Int. Cl.
*A61B 5/11* (2006.01)
*G06T 17/20* (2006.01)
(52) U.S. Cl.
CPC .......... *A61B 5/1124* (2013.01); *A61B 5/1128* (2013.01); *A61B 5/7275* (2013.01); *G06T 7/20* (2013.01); *G06T 17/20* (2013.01); *G06T 2207/20081* (2013.01); *G06T 2207/20084* (2013.01); *G06T 2207/30004* (2013.01); *G06T 2210/12* (2013.01); *G06T 2210/41* (2013.01)
(58) Field of Classification Search
CPC ......... A61B 5/7275; G06T 7/20; G06T 17/20; G06T 2207/20081; G06T 2207/20084; G06T 2207/30004; G06T 2210/12; G06T 2210/41

See application file for complete search history.

(56) References Cited

U.S. PATENT DOCUMENTS

| | | | | |
|---|---|---|---|---|
| 2012/0253201 | A1* | 10/2012 | Reinhold | H04N 13/254 345/419 |
| 2018/0060653 | A1* | 3/2018 | Zhang | G06V 20/52 |
| 2019/0110736 | A1* | 4/2019 | Broderick | G06T 7/246 |
| 2019/0371080 | A1* | 12/2019 | Sminchisescu | G06T 17/20 |
| 2020/0160044 | A1* | 5/2020 | Sur | G16H 50/50 |
| 2020/0302245 | A1* | 9/2020 | Zia | G06F 18/214 |
| 2021/0201075 | A1* | 7/2021 | Pahde | G06T 17/20 |
| 2021/0307621 | A1* | 10/2021 | Svenson | A61B 5/02416 |
| 2021/0315486 | A1* | 10/2021 | Delp | G16H 50/50 |

OTHER PUBLICATIONS

Andriluka et al., "2D Human Pose Estimation: New Benchmark and State of the Art Analysis", 2014 IEEE Conference on Computer Vision and Pattern Recognition, 2014, pp. 3686-3693.

Bewley et al., "Simple online and realtime tracking", 2016 IEEE International Conference on Image Processing (ICIP), Sep. 25-28, 2016, pp. 3464-3468, arXiv:1602.00763 [cs.CV], Jul. 7, 2017, DOI: 10.1109/ICIP.2016.7533003.

Bharti et al., "Neuroimaging advances in Parkinson's disease with freezing of gait: A systematic review", NeuroImage Clinical, 2019, vol. 24, 102059, online publication Nov. 9, 2019, 16 pgs., doi: 10.1016/j.nicl.2019.102059.

Bogo et al., "Keep it SMPL: Automatic Estimation of 3D Human Pose and Shape from a Single Image", Jul. 2016, arXiv: 1607 . . . 08128 [cs.CV], Jul. 27, 2016, 561-578.

Cao et al., "Realtime Multi-Person 2D Pose Estimation using Part Affinity Fields", arXiv:1611.08050v2 [cs.CV], Apr. 14, 2017, 9 pgs.

Chiu et al., "Action-Agnostic Human Pose Forecasting", arXiv:1810.09676 [cs.CV], Oct. 23, 2018, 10 pgs.

Cho et al., "A vision-based analysis system for gait recognition in patients with Parkinson's disease", Expert Systems with Applications, Apr. 2009, vol. 36, Issue 3, Part 2, pp. 7033-7039, https://doi.org/10.1016/j.eswa.2008.08.076.

Evers et al., "Measuring Parkinson's disease over time: The real-world within-subject reliability of the MDS-UPDRS", Movement Disorders, 2019, vol. 34, No. 10, pp. 1480-1487, published online Jul. 10, 2019, DOI: 10.1002/mds.27790.

Goetz et al., "Movement Disorder Society-Sponsored Revision of the Unified Parkinson's Disease Rating Scale (MDS-UPDRS): Scale Presentation and Clinimetric Testing Results", Movement Disorders, 2008, vol. 23, No. 15, pp. 2129-2170, first published Nov. 24, 2008, https://doi.org/10.1002/mds.22340.

Han et al., "Gait detection from three dimensional acceleration signals of ankles for the patients with Parkinson's disease", Proceedings of the IEEE The International Special Topic Conference on Information Technology in Biomedicine, Ioannina, Epirus, Greece, 2006, vol. 2628, 4 pgs.

Hobert et al., "Progressive Gait Deficits in Parkinson's Disease: A Wearable-Based Biannual 5-Year Prospective Study", Frontiers in Aging Neuroscience, Feb. 2019, vol. 11, No. 22, pp. 1-7, DOI:10.3389/fnagi.2019.00022.

Hssayeni et al., "Wearable Sensors for Estimation of Parkinsonian Tremor Severity during Free Body Movements", Sensors, Sep. 28, 2019, vol. 19, No. 19, 4215, pp. 1-17, doi: 10.3390/s19194215.

Ionescu et al., "Human3.6M: Large Scale Datasets and Predictive Methods for 3D Human Sensing in Natural Environments", IEEE Transactions on Pattern Analysis and Machine Intelligence, Jul. 2014, vol. 36, Issue 7, pp. 1-15, published online Dec. 12, 2013, DOI: 10.1109/TPAMI.2013.248.

Kalman, "A New Approach to Linear Filtering and Prediction Problems", Transactions of the ASME—Journal of Basic Engineering, 1960; vol. 82, (Series D), pp. 35-45.

Kingma et al., "Adam: A Method for Stochastic Optimization", arXiv.org, Retrieved from: https://arxiv.org/abs/1412.6980v1 [cs.LG], Dec. 22, 2014, 9 pgs.

Kolotouros et al., "Learning to Reconstruct 3D Human Pose and Shape via Model-Fitting in the Loop", 2019 IEEE/CVF International Conference on Computer Vision (ICCV), Oct. 2019, 10 pgs., DOI:10.1109/ICCV.2019.00234.

Kuhn, "The Hungarian method for the assignment problem", Naval Research Logistics Quarterly, Mar. 1955, vol. 2, Issue 1-2, pp. 83-97.

Lin et al., "Focal Loss for Dense Object Detection", 2017 IEEE International Conference on Computer Vision (ICCV), pp. 2980-2988, Oct. 22-29, 2017, DOI: 10.1109/ICCV.2017.324.

Loper et al., "SMPL: a skinned multi-person linear model", ACM Transactions on Graphics, Nov. 2015, vol. 34, No. 6, pp. 1-16, DOI:10.1145/2816795.2818013.

Mehta et al., "VNect: Real-time 3D Human Pose Estimation with a Single RGB Camera", ACM Transactions on Graphics, Jul. 2017, vol. 36, No. 4, pp. 1-14, DOI: 10.1145/3072959.3073596.

Pang et al., "DeepRank: A New Deep Architecture for Relevance Ranking in Information Retrieva", Proceedings of the 2017 ACM on Conference on Information and Knowledge Management, Nov. 6-10, 2017, Singapore, 10 pgs., DOI: dx.doi.org/10.1145/3132847.3132914.

Poston et al., "Compensatory neural mechanisms in cognitively unimpaired Parkinson disease", Annals of Neurology, 2016, vol. 79, pp. 448-463, first published Dec. 22, 2015, https://doi.org/10.1002/ana.24585.

Rennie et al., "Loss functions for preference levels: Regression with discrete ordered labels", In: IJCAI workshop advances in preference handling, Jan. 2005, 6 pgs.

Venuto et al., "A review of disease progression models of Parkinson's disease and applications in clinical trials", Movement Disorders, Jul. 2016, vol. 31, Issue 7, pp. 947-956, first published May 26, 2016, https://doi.org/10.1002/mds.26644.

Wang et al., "Silhouette Analysis-Based Gait Recognition for Human Identification", IEEE Transactions on Pattern Analysis and Machine Intelligence, Dec. 2003, vol. 25, No. 12, pp. 1505-1518.

Xue et al., "Vision-Based Gait Analysis for Senior Care", arXiv:1812.00169 [cx.CV], Dec. 1, 2018, 5 pgs.

Yang et al., "Make Skeleton-based Action Recognition Model Smaller, Faster and Better", ACM Multimedia Asia, Dec. 2019, 6 pgs., DOI:10.1145/3338533.3366569.

Kanazawa et al., "End-to-end Recovery of Human Shape and Pose", CVPR, 2018, pp. 7122-7131.

\* cited by examiner

SYSTEMS AND METHODS FOR ESTIMATION OF PARKINSON'S DISEASE GAIT IMPAIRMENT SEVERITY FROM VIDEOS USING MDS-UPDRS

CROSS-REFERENCE TO RELATED APPLICATIONS

This application claims priority to U.S. provisional patent application Ser. No. 63/037,526 entitled "Estimation of Parkinson's Disease Gait Impairment Severity from Videos Using MDS-UPDRS," filed on Jun. 10, 2020, which is incorporated by reference herein in its entirety.

STATEMENT OF FEDERAL FUNDING

This invention was made with Government support under contracts AA010723 and AG047366 awarded by the National Institutes of Health. The Government has certain rights in the invention.

FIELD OF THE INVENTION

The present invention is related to estimation of Parkinson's Disease severity from videos using MDS-UPDRS.

BACKGROUND

Parkinson's disease (PD) is a brain disorder that primarily affects motor function, leading to slow movement (bradykinesia), tremor, and stiffness (rigidity), as well as postural instability and difficulty with walking/balance. PD is the second most prevalent neurodegenerative disease. PD is caused by a gradual decline in dopamine production, resulting in progressive deterioration of selective brain neurons. The degeneration of dopamine-containing cells in the basal ganglia regions provoke visible signs of gait disturbances and postural instabilities. Early PD diagnosis and tracking of its signs are crucial for the development and maintenance of treatment plans.

The severity of PD motor impairments is clinically assessed by part Ill of the Movement Disorder Society Unified Parkinson's Disease Rating Scale (MDS-UPDRS), a universally-accepted rating scale. MDS-UPDRS defines the most commonly used clinical scoring scheme to measure the severity and progression of PD However, experts often disagree on the exact scoring of individuals. Accurate and quantitative assessment of disease progression is critical to developing treatment that slows or stops further advancement of disease.

SUMMARY OF THE INVENTION

Systems and methods in accordance with various embodiments of the invention provide for evaluation motion from a video. In an embodiment, the system includes, identifying a target individual in a set of one or more frames in a video, analyzing the set of frames to determine a set of pose parameters, generating a 3D body mesh based on the pose parameters, identifying joint positions for the target individual in the set of frames based on the generated 3D body mesh, predicting a motion evaluation score based on the identified join positions, and providing an output based on the motion evaluation score.

In a further embodiment, identifying a target individual includes: tracking a plurality of individuals in each frame of the set of frames; and identifying an individual that appears most often in the set of frames as the target individual.

In a further embodiment again, identifying a target individual includes identifying a bounding box for the target individual in each of the set of frames, where analyzing the set of frames includes analyzing the bounding box in each of the set of frames.

In still a further embodiment, predicting the motion evaluation score is performed using a score evaluation model, where the score evaluation model is trained using a hybrid ordinal-focal objective.

In still a further embodiment again, the score evaluation model takes as input at least one of a joint collection distance (JCD) and two-scale motion features.

In yet a further embodiment again, the JCD and two-scale motion features are embedded into latent vectors at each frame through a series of convolutions to learn joint correlation and reduce the effect of skeleton noise.

In a further additional embodiment again, the motion evaluation score is a Movement Disorder Society Unified Parkinson's Disease Rating Scale (MDS-UPDRS) gait score.

In a further embodiment, the system further includes using a trained temporal convolutional neural network (TCNN) on the sequence of 3D poses to quantify movement-linked disease markers.

In still a further embodiment, the TCNN uses a Rater Confusion Estimation (RCE) framework that jointly leans a rater scoring noise by creating a learnable confusion matrix (CM) for each rater, and wherein the method optimizes the CM while classifying input videos using an ordinal focal strategy.

BRIEF DESCRIPTION OF THE DRAWINGS

The description will be more fully understood with reference to the following figures and data graphs, which are presented as various embodiments of the disclosure and should not be construed as a complete recitation of the scope of the disclosure, wherein.

DETAILED DESCRIPTION

Many embodiments provide for systems and methods for assessing disease based on computer video analysis of patient recordings. In particular, many embodiments provide for a computer vision-based model that can observe non-intrusive video recordings of individuals, extract their 3D body skeletons, track the individuals through space and time, and provide information that can be used to diagnose and/or classify a disease and/or a severity or progression of a disease. In particular, many embodiments of the system can be used to determine a severity of Parkinson's disease (PD) according to standard MDS-UPDRS classes.

Many prior techniques for treating Parkinson's have been based on neuroimages or largely rely on quantifying motor impairments via wearable sensors that can be expensive, unwieldy, and intrusive. Accordingly, many embodiments of the system are able to asses PD using video-based technologies and machine learning in order to provide non-intrusive and scalable ways of quantifying human movements, that can be applied to any of a variety of clinical applications, including PD.

Systems and methods in accordance with certain embodiments of the invention can assess PD severity related to gait and posture impairments based on videos. Although there exist a few video-based methods which assess gait for PD diagnosis, processes in accordance with various embodiments of the invention can define a new task and a principled benchmark by estimating the standard MDS-UPDRS scores. There are several challenges to this new setting: (1) there are no baselines to build upon; (2) since it is harder to recruit patients with severe impairments, the number of participants in the dataset can be imbalanced across MDS-UPDRS classes; (3) clinical datasets are typically limited in the number participants, presenting difficulty for training deep learning models; (4) estimating MDS-UPDRS scores defines a multi-class classification problem on a scale of scores from 0 to 4, while prior work only focused on diagnosing PD vs. normal. To address these challenges, 3D pose estimation models in accordance with many embodiments of the invention can be trained on large public datasets. In some embodiments, trained models can be used to extract 3D poses (3D coordinates of body joints) from clinical data. Therefore, estimation of the MDS-UPDRS scores in accordance with several embodiments of the invention can be performed on low-dimensional pose data which can be agnostic to the clinical environment and the video background. To deal with data imbalance, models in accordance with certain embodiments of the invention can use a focal loss. In certain embodiments, focal loss can be coupled with an ordinal loss component to enforce the order present in the MDS-UPDRS scores.

Many embodiments of the system can capture monocular videos of the MDS-UPDRS gait exam as an input and automatically estimate each participants' gate score on the MDS-UPDRS standard scale. In particular, many embodiments can identify and track a participant in a video, extract a 3D skeleton (e.g., pose) from each video frame, and train a temporal convolutional neural network (TCNN) on the sequence of 3D poses by training a Double-Features Double-Motion Network (DD-NET) with a hybrid ordinal-focal objective, referred to as a hybrid Ordinal Focal DDNet (OF-DDNET).

Medical experts may often disagree on exact PD scores for individuals, which can be problematic for providing a labeled data set that can be used for machine learning. In the presence of label noise, training a machine learning model using only scores from a single rater may introduce bias, while training models with multiple noisy ratings can be a challenging task due to the inter-rater variabilities. Accordingly, many embodiments of the machine learning system provide for an ordinal focal neural network to estimate the MDS-UPDRS scores from input videos, to leverage the ordinal nature of MDS-UPDRS scores and combat class imbalance. To handle multiple noisy labels per exam, the training of the network in accordance with many embodiments of the invention can be regularized via rater confusion estimation (RCE), which may encode the rating habits and skills of raters via a confusion matrix. Many embodiments of the system can be used to estimate MDS-UPDRS gait scores (with multiple Raters, R=3) and MDS-UPDRS finger tapping scores (single rater).

Figure 1:
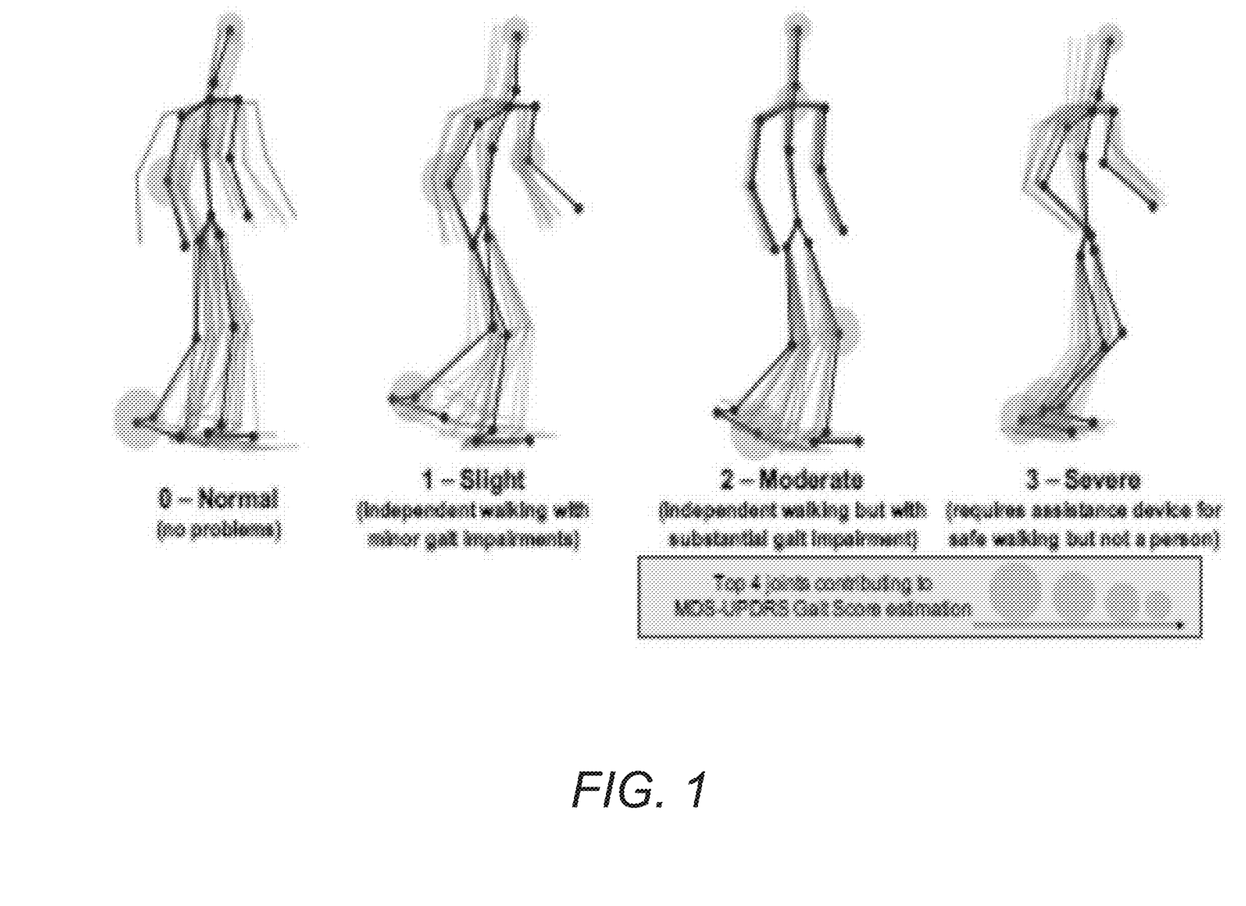
FIG. 1 conceptually illustrates progressive PD impairments demonstrated by 3D gait (poses fade over time; left/right distinguished by color) with MDS-UPDRS gait score shown below each skeleton in accordance with an embodiment of the invention.

MDS-UPDRS can include several tests measuring different aspects of movement, including a gait test and a finger tapping test. The MDS-UPDRS gait test requires a participant to walk approximately 10 meters away from and toward an examiner. Trained specialists assess the participant's posture with respect to movement and balance (e.g., 'stride amplitude/speed,' 'height of foot lift,' 'heel strike during walking,' 'turning,' and 'arm swing') by observation. The score can range from 0 indicating no motor impairments to 4 for patients unable to move independently, as illustrated in FIG. 1 in accordance with an embodiment of the invention. In particular, FIG. 1 illustrates progressive PD impairments demonstrated by 3D gait (poses fade over time; left/right distinguished by color) with MDS-UPDRS gait score shown below each skeleton. Scores 0 to 2 progressively decrease in mobility with reduced arm swing and range of pedal motion (e.g, reduced stride amplitude and footlift) while 3 can become imbalanced with almost frozen gait. The average movements can be the outputs of the proposed pipeline in accordance with many embodiments. The top four joints which can contribute to gait score estimation are indicated in FIG. 1.

For the MDS-UPDRS finger tapping tests, participants are asked to tap their index finger to their thumb 10 times as quickly and as big as possible. It is used to measure the motor speed and amplitude of the index finger as a subtle and indirect estimate of cortical motor areas integrity. MDS-UPDRS tests can provide principled and well-defined platforms for quantifying PD motor severity.

In many embodiments of the machine learning (ML) system, videos of these tests can be automatically processed to quantify movement-linked disease markers. Many embodiments of the system can quantify movement-linked impairments for assessing PD severity on universally-accepted scales (e.g., MDS-UPDRS). Many embodiments can use videos of participants performing the maneuvers of the MDS-UPDRS and can define a new task and a principled benchmark by estimating the standard clinical scores. However, a challenge can be the possible subjective opinions of clinical raters (rating participants using the MDS-UPDRS scale), which may in turn bias the machine learning model to rating habits or subjective opinion of a single rater.

To avoid these challenges, many embodiments of the system can leverage ratings from multiple expert neurologists to build a robust score estimation model agnostic to single rater habits or preferences. Incorporating ratings from multiple raters can introduce a source of uncertainty and noise. Certain embodiments can use information that estimates the skills of raters (or data annotators) while teaching the model to classify the data. The extra knowledge of the rater skills or habits can be additional information for discovering how confident the ratings from a rater for each input sample should be considered. Therefore, accurately modeling the uncertainty (or noise) induced by the ratings of each rater can be useful for improving the accuracy of the final model as well as understanding the quality of the scoring. Accordingly, many embodiments of the system can use a Rater Confusion Estimation (RCE) framework that jointly learns the rater scoring noise and MDS-UPDRS score estimation. Several embodiment of the system can create a learnable confusion matrix (CM) for each rater and optimize for it while classifying the input videos using an ordinal focal strategy (to comply with the ordinal nature of MDS-UPDRS scores and combat small dataset size). The system in accordance with several embodiments can regularize a model within this joint training framework to encourage the estimated raters' noise to be maximally unreliable, e.g., considering the raters to be maximally uncertain to learn a robust classifier. The model hence can learn to discard the unreliable ratings.

Many embodiments of the ML classification model can be applied on skeletons of the participants extracted from a video (skeleton extraction can be pretrained on large public datasets). In many embodiments, the estimation of the MDS-UPDRS scores can be performed on low-dimensional skeletons (e.g., 49 keypoints/joints in 3D space for gait and 21 hand keypoints), which anonymizes the data and makes it agnostic to the clinical environment and video background. In many embodiments of the ML system, in addition to the gait test, the system can be used on the MDS-UPDRS Finger Tapping test scores to evaluate bradykinesia by measuring decrements in rate, amplitude, or both.

Label Uncertainty

Label noise can greatly affect the efficacy of machine and deep learning models, especially in medical applications, which often have small datasets, require domain expertise and suffer from high inter-rater and intra-rater variability. Many techniques have been explored to handle this variability, such as label cleaning and changes in network architecture changes. Numerous studies have proposed to keep the initial dataset, modeling, and training methods intact while only changing the loss function. Specifically focusing on the case with scores from multiple medical experts, proposed an annotator confusion estimation method, which learns rater confusion matrices jointly with the correct label during training.

Many embodiments of the system analyze sections of a participant videos documenting the finger tapping examination, in which participants are instructed to tap the index finger on the thumb 10 times as quickly and as big as possible. Each hand can be rated separately in evaluating speed, amplitude, hesitations, halts, and decrementing amplitude. The finger tapping clips can range from a few seconds (e.g., 4 seconds to 30 seconds) with 30 frames per second.

In both gait and finger tapping experiments, participants who cannot perform the test at all or without assistance are scored 4.

Estimation of MDS-UPDRS Scores from Videos

Figure 2:
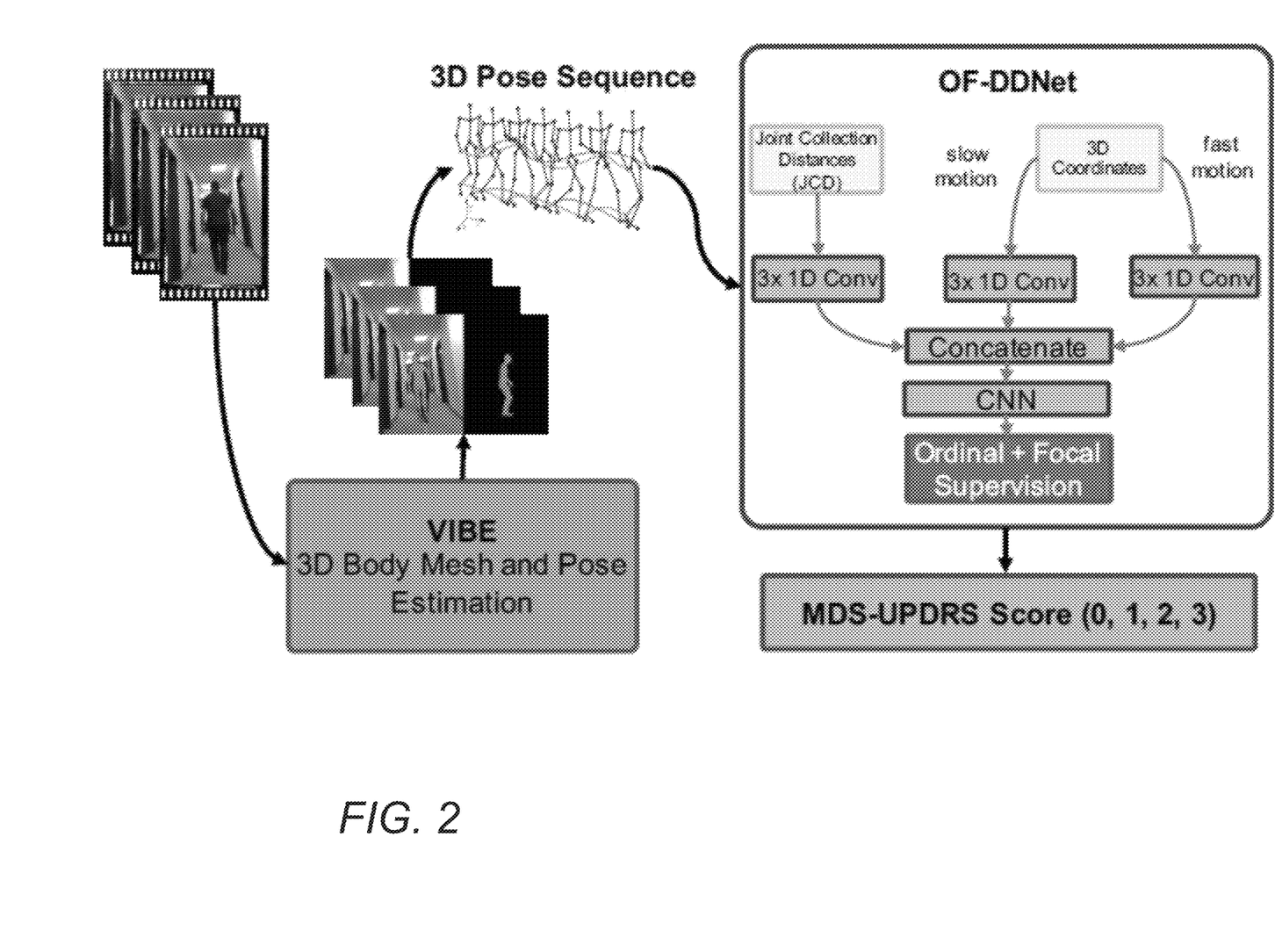
FIG. 2 conceptually illustrates a framework for estimating scores from videos in accordance with an embodiment of the invention.

FIG. 2 illustrates a framework for estimating scores from videos in accordance with an embodiment of the invention. The system can extract the identified participants' 3D body mesh and subsequently the skeletons via VIBE (e.g., Video Inference for human Body pose and Shape Estimation). Based on this 3D skeleton sequence, the OF-DDNet can estimate the MDS-UPDRS gait score.

As shown in FIG. 2, a monocular video of the participant walking in the scene forms the input. The system can include two main steps, a 3D skeleton extraction and a motor score estimation.

First, each participant in the video can be tracked (e.g., using theSORT (simple online and realtime tracking) algorithm) and bounding boxes corresponding to the participant can be identified. In a variety of embodiments, bounding boxes along with the MDS-UPDRS exam video frames can be passed to a trained 3D pose extraction model (e.g., SPIN), which can provide pose inputs to OF-DDNet.

Processes in accordance with a variety of embodiments of the invention can detect and track a participant since videos may contain multiple other people (e.g., clinicians and nurses). To do this, the system can track each participant in the video (e.g., with SORT, a real-time tracking algorithm for 2D multiple object tracking in video sequences. SORT may use a Faster Region CNN (FrRCNN) as a detection framework, a Kalman filter as the motion prediction component, and the Hungarian algorithm for matching the detected boxes. In numerous embodiments, the participant is assumed to be in all frames and, hence, the system can pick the tracked person who is consistently present in all frames and has the greatest number of bounding boxes as the patient.

Skeleton Extraction—GAIT

As noted above, many embodiments of the system can extract a 3D skeleton from the gait videos with VIBE (Video Inference for human Body pose and shape Estimation). This can be an extension of SPIN (SMPL oPtimization IN the loop), a neural method for estimating 3D human skeleton and shape from 2D monocular images of an input video. In many embodiments, the system can be initialized with pretrained SMPL. The pipeline can first recover the 3D body mesh using Human Mesh Recovery (HMR) pretrained on the large publicly-available Human and MPI-INF-3DHP datasets, providing over 150 k training images with 3D joint annotations, as well as large-scale datasets with 2D annotations. In many embodiments, the process can reduce the videos to 3D human meshes and regresses them to skeletons with a number (e.g., 49) of predefined joints.

3D Body Mesh and Pose Extraction

As illustrated in FIG. 2, in several embodiments, the system can extract 3D pose from each frame using the image at each frame and the participant bounding box found in the previous step as input to a model for estimating 3D human pose and shape from 2D monocular images (SPIN (SMPL oPtimization IN the loop)). Based on a single 2D image, predictions for pose parameters $\theta_{reg}$, shape parameters $\beta_{reg}$, camera parameters $\Pi_{reg}$, 3D joints $X_{reg}$ of the mesh and their 2D projection $J_{reg}=\Pi_{reg}(X_{reg})$ can be predicted (using the Human Mesh Recovery (HMR) regressor). In certain embodiments, following the optimization routine (e.g., SMPLify), these can be initial parameters for the SMPL body model, a function $M(\theta, \beta)$ of pose parameters $\theta$ and shape parameters $\beta$ that returns the body mesh. In many embodiments, a linear regressor W can perform regressions on the mesh to find 3D joints $J_{smpl}$. These regressed joint values can be supplied to the iterative fitting routine in accordance with various embodiments of the invention, which encourages the 2D projection of the SMPL joints $J_{smpl}$ to align with the annotated 2D keypoints $J_{reg}$ by penalizing their weighted distance. The fitted model can be subsequently used as supervision for the regressor, forming an iterative training loop. In certain embodiments, the system can generate 3D pose for each video frame by performing regression on the 3D mesh output from SMPL, which has been fine-tuned in the SPIN loop. In certain embodiments, SPIN can be initialized with pretrained SMPL and HMR pretrained on the large Human3.6M and MPI-INF-3DHP datasets, providing over 150 k training images with 3D joint annotations, as well as large-scale datasets with 2D annotations (e.g., COCO and MPII). Although FIG. 2 illustrates a particular framework for extracting a participants' 3D body mesh and skeletons and based on the 3D skeleton sequence, estimating MDS-UPDRS gait score using OF-DDNet, any of a variety of architectures can be utilized as appropriate to the requirements of specific applications in accordance with embodiments of the invention. Video based analysis for specific body parts, including the finger tapping test are described below.

Hand

Many embodiments of the system can extract 2D hand skeleton from finger tapping videos with the OpenPose hand keypoint detection system, which produces a number (e.g., 21) keypoints for each of the right and left hands. This system can use the training process, multiview bootstrapping with multiple cameras, to produce fine-grained detectors for hand keypoints with greater robustness to noise and occlusion. In many embodiments, a keypoint detector is first initialized to produce noisy scores in multiple views of the hand, which are triangulated in 3D and reprojected to be used iteratively as new scores during training. Many embodiments may use this hand detection model for the finger tapping experiment because it is a single-view image-based hand keypoint detector comparable to methods that use depth sensors. It can produce numerous and precise hand keypoints that are crucial to representing fine hand movements and hence quantify PD motor impairments.

Score Estimation from Skeletons Based on Single Rater Scores

Feature Construction

Many embodiments of the system transform the skeleton data and their movement over time in a video clip into a series of features as the input to the classification model. Two types of features can be used to address the variance of 3D Cartesian joints to both location and viewpoint: (1) Joint Collection Distances (JCD) and (2) two-scale motion features.

Let $J_j^t$ be the 3D Cartesian coordinates of the $j^{th}$ joint at frame t, where $j \in \{1, \ldots, n\}$ and $t \in \{1, \ldots, T\}$. JCD is then defined as a location-viewpoint invariant feature that represents the Euclidean distances between joints as a matrix M, where $M_{jk}^t = \|J_j^t - J_k^t\|$ for joints j and k at frame t. Since M is a symmetric matrix, only the upper triangular matrix is preserved and flattened to a dimension of $$\binom{n}{2}$$

for n joints. A two-scale motion feature is introduced for global scale invariance which measures temporal difference between nearby frames. To capture varying scales of global motion, many embodiments calculate slow motion ($M_{slow}^t$) and fast motion ($M_{fast}^t$)

$$M_{slow}^t = S^{t+1} - S^t, t \in \{1,2,3, \ldots, T-1\},$$

$$M_{fast}^t = S^{t+2} - S^t, t \in \{1,3,5, \ldots, T-2\}, \quad (1)$$

where $S^t = \{j_1^t, J_2^t, \ldots J_n^t\}$ denotes the set of joints for the $t^{th}$ frame. The JCD and two-scale motion features can be embedded into latent vectors at each frame through a series of convolutions to learn joint correlation and reduce the effect of skeleton noise. Then, for the $i^{th}$ video clip, the embeddings can be concatenated and run through a series of 1D temporal convolutions and pooling layers, culminating with a softmax activation on the final layer to output a probability for each of the C classes $p_i = [p_{i,1}, \ldots, p_{i,C}]^T$, as illustrated in FIG. 2 in accordance with an embodiment of the invention. In situations where there may be a relatively small clinical dataset compared to large deep learning datasets, many embodiments of the system choose a lightweight temporal CNN-based architecture that prevents overfitting. Although FIG. 2 illustrates a particular framework for extracting a participants 3D body mesh and skeletons and estimating an MDS-UPDRS gait score using OF-DDNet, any of a variety of frameworks can be utilized as appropriate to the requirements of specific applications in accordance with embodiments of the invention.

Hybrid Ordinal-Focal (OF) Loss

Many embodiments of the system can leverage the ordinal nature of MDS-UPDRS scores to combat the natural class imbalance in clinical dataset by proposing a hybrid ordinal (O) focal (F) loss. One of the use cases of the focal loss has been to combat class imbalance. It can be used for binary classification, but it is naturally extensible to multi-class classification (e.g., C>2 classes). Let $y_i = [y_{i,1}, \ldots, y_{i,C}]$ be the one-hot-encoding label for the score of the $i^{th}$ training sample. The focal loss is then defined as $$F(y_i, p_i) = \sum_{c=1}^{C} -\alpha(1 - p_{i,c})^{\gamma} y_{i,c} \log(p_{i,c}).$$

The modulating factor $(1-p_{i,c})^{\gamma}$ is small for easy negatives where the model has high certainty and close to 1 for misclassified examples. This combats class imbalance by down-weighting learning for easy negatives, while preserving basic cross-entropy loss for misclassified examples. Many embodiments can set the default focusing parameter of $\gamma=2$ and weighting factor $\alpha=0.25$.

To leverage the intrinsic order in the MDS-UPDRS scores, many embodiments of the system can use an ordinal loss, which penalizes predictions more if they are violating the order. Let $y_i = \text{argmax}_c \{y_{i,c}\}$ be the actual score for the $i^{th}$ video ($y_i \in \{0,1,2,3\}$), and let $\hat{y}_i \in \{0,1,2,3\}$ be the estimated score. Many embodiments can calculate the absolute distance $w_i = |y_i - \hat{y}_i|$ and incorporate this with categorical cross-entropy to generate the ordinal loss:

$$O(y_i, p_i) = -\frac{1 + w_i}{C} \sum_{c=1}^{C} y_{i,c} \log(p_{i,c}).$$

In many embodiments, ordinal and focal losses can be naturally combined by factorizing them with scaling factor $\beta$ for the ordinal component as $$OF(y_i, p_i) = -\sum_{c=1}^{C} \left( \alpha(1 - p_{i,c})^{\gamma} + \beta \frac{1 + w_i}{C} \right) y_{i,c} \log(p_{i,c}). \quad (2)$$

Multiple Rater Scores

In the presence of uncertainty in the label (score) space (MDS-UPDRS Gait scores provided by different raters), many embodiments of the system can provide an extension to the OF loss. Many embodiments can include a rater confusion data-weighting and loss scheme. In this framework, the system can learn both the OF-DDNet model parameters and scoring patterns of each rater, akin to a rater profile. Each scoring profile can be encoded as a confusion matrix (CM) utilized by the Rater Confusion Estimation (RCE) technique described in detail throughout.

Assume there are noisy scores $\{y_i^{(r)}\}$ from R different raters, where $r \in \{1, \ldots, R\}$ (R is the total number of raters).

Figure 3:
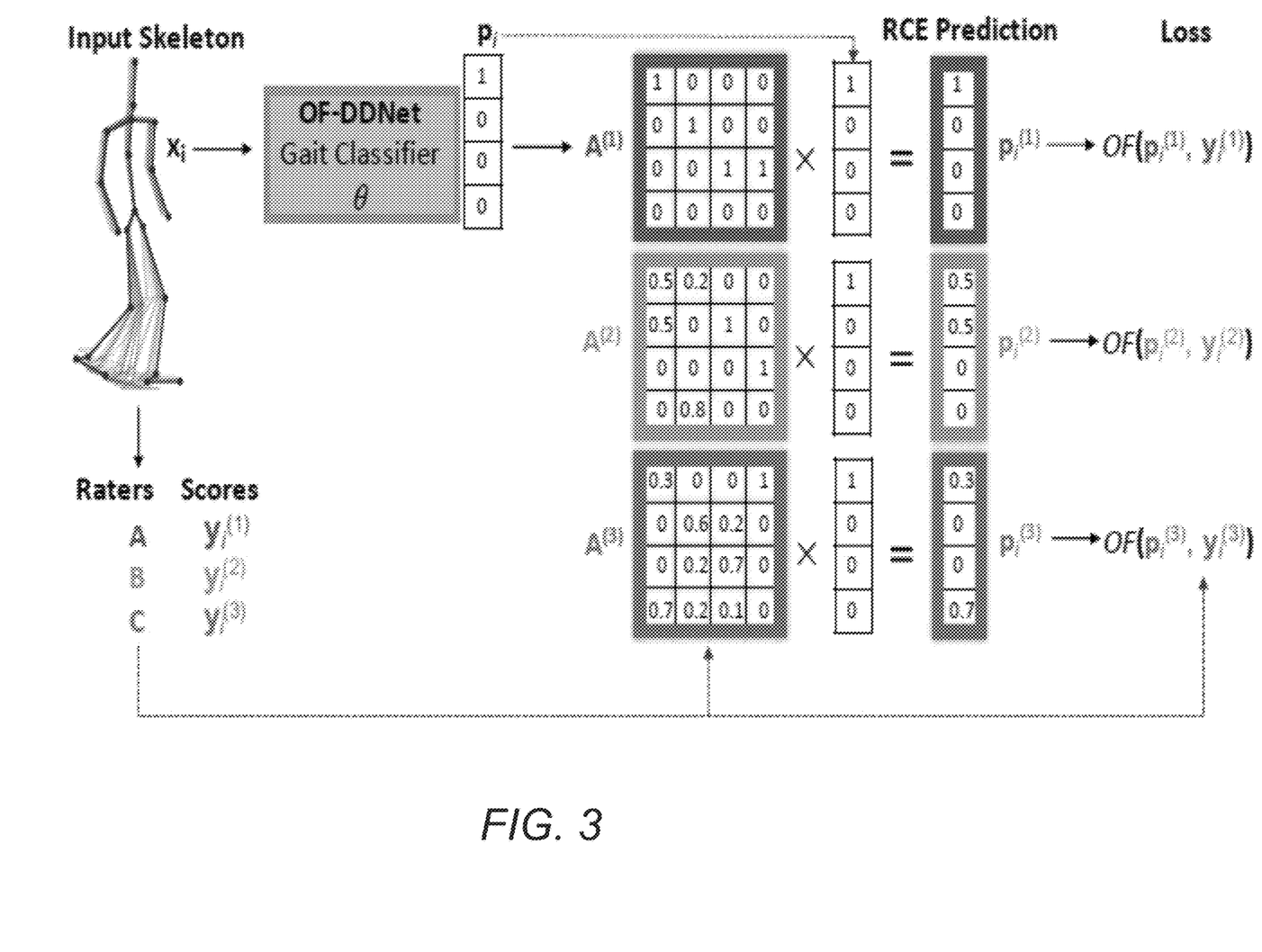
FIG. 3 illustrates an OF-DDNet training pipeline with Rater Confusion Estimation (RCE) in accordance with an embodiment of the invention.

Many embodiments construct a confusion matrix $A^{(r)}$ for rater r, where the (c', c) entry of the matrix is the probability $p(y_i^{(r)}=c' | y_i=c)$, e.g., the probability that rater r corrupts the ground-truth score $y_i=c$ to $y_i^{(r)}=c'$. Note, this probability can be independent of the input image and solely characterizes the systematic bias of rater r in scoring videos. Assuming $p_i$ is the true class probability vector for the $i^{th}$ video estimated by the model, the RCE-weighted prediction $p_i^{(r)}=A^{(r)}p_i$ is then the estimated class probability vector weighted by the confusion matrix of rater r, as illustrated in FIG. 3 in accordance with an embodiment of the invention. In particular FIG. 3 illustrates an OF-DDNet training pipeline with Rater Confusion Estimation (RCE). In many embodiments, this is implemented for the gait MDS-UPDRS score estimation with a number of raters (e.g, 3). Given a series of input skeletons, OF-DDNet can generate prediction $p_i$ for the input. This prediction can be multiplied by each rater CM $A^{(r)}$ to produce a prediction for each rater. The total loss is the sum of the individual losses between each ($p_i^{(r)}$, $y_i^{(r)}$) pair of the $r^{th}$ rater.

As such, the true scores and confusion matrices can be jointly optimized with the OF loss function $$\sum_{i=1}^{N} \sum_{r=1}^{R} OF(p_i^{(r)}, y_i^{(r)}) + \lambda \sum_{r=1}^{R} tr(A^{(r)}), \quad (3)$$

When $\{A^{(r)}\}$ are initialized as identity matrices, a trace regularization $$\lambda \sum_{r=1}^{R} tr(A^{(r)})$$

can be used in practice to find the maximal amount of confusion to best explain the noisy observations.

To implement the optimization defined in Eq. (3), many embodiments may ensure that each column of $A^{(r)}$ defines a conditional probability that sums up to 1. This constraint can be satisfied by projecting the columns of $A^{(r)}$ onto a simplex in each optimization iteration via an explicit projection operation. To this end, before calculating the loss for each training step, many embodiments set $$A_{ij}^{(r)} := \frac{A_{ij}^{(r)}}{\sum_{k=1}^{C} A_{kj}^{(r)}}. \quad (4)$$

EXPERIMENTS

Many embodiments can process a dataset by first subclipping each video into shorter samples and then normalizing joints per clip after skeleton extraction. The gait exams can be subclipped into samples of 100 frames each, creating multiple subclips from each single exam video. The finger tapping subclips can start at multiples of 80 frames offset from the beginning of the exam and finish at the end of the exam. Due to clips containing overlapping components, many embodiments can add Gaussian noise to each subclip distributed as N(0,0.02). During training, the ground-truth score of each subclip can be the same as the score of the exam. During evaluation, the predicted score of an exam can be the majority vote among its subclips. This subclipping and subvoting mechanism can add robustness to the overall system and allows for augmenting the dataset for proper training of the OF-DDNet.

Figure 4:
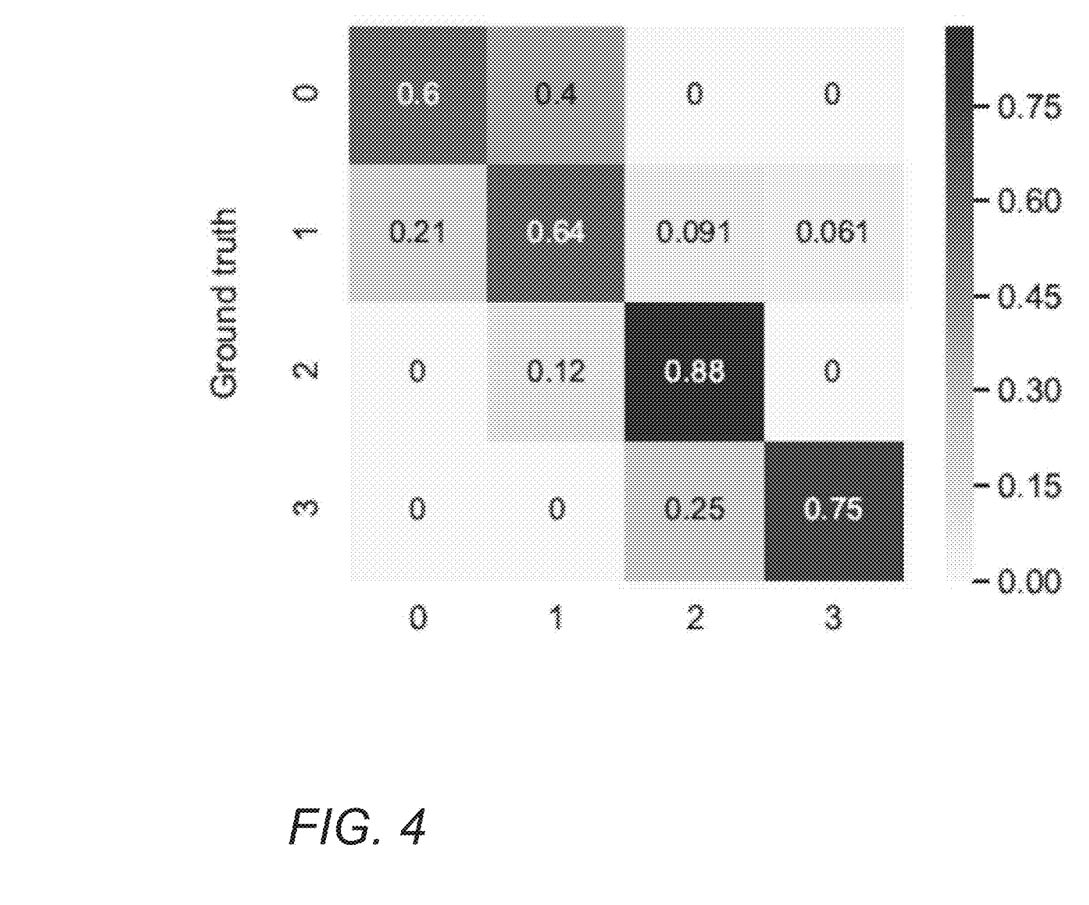
FIG. 4 illustrates a confusion matrix of a model for estimation of MDS-UPDRS gait scores in accordance with an embodiment of the invention.

FIG. 4 illustrates a confusion matrix of a model for estimation of MDS-UPDRS gait scores in accordance with an embodiment of the invention.

As seen in the confusion matrix illustrated in FIG. 3, all errors are within one score deviation of the ground-truth (based on majority vote), with the exception of a small portion of score 1 misclassified as score 3. This indicates that the model successfully forms predictions within a range very similar to the raters themselves.

Model Interpretation.

Figure 5:
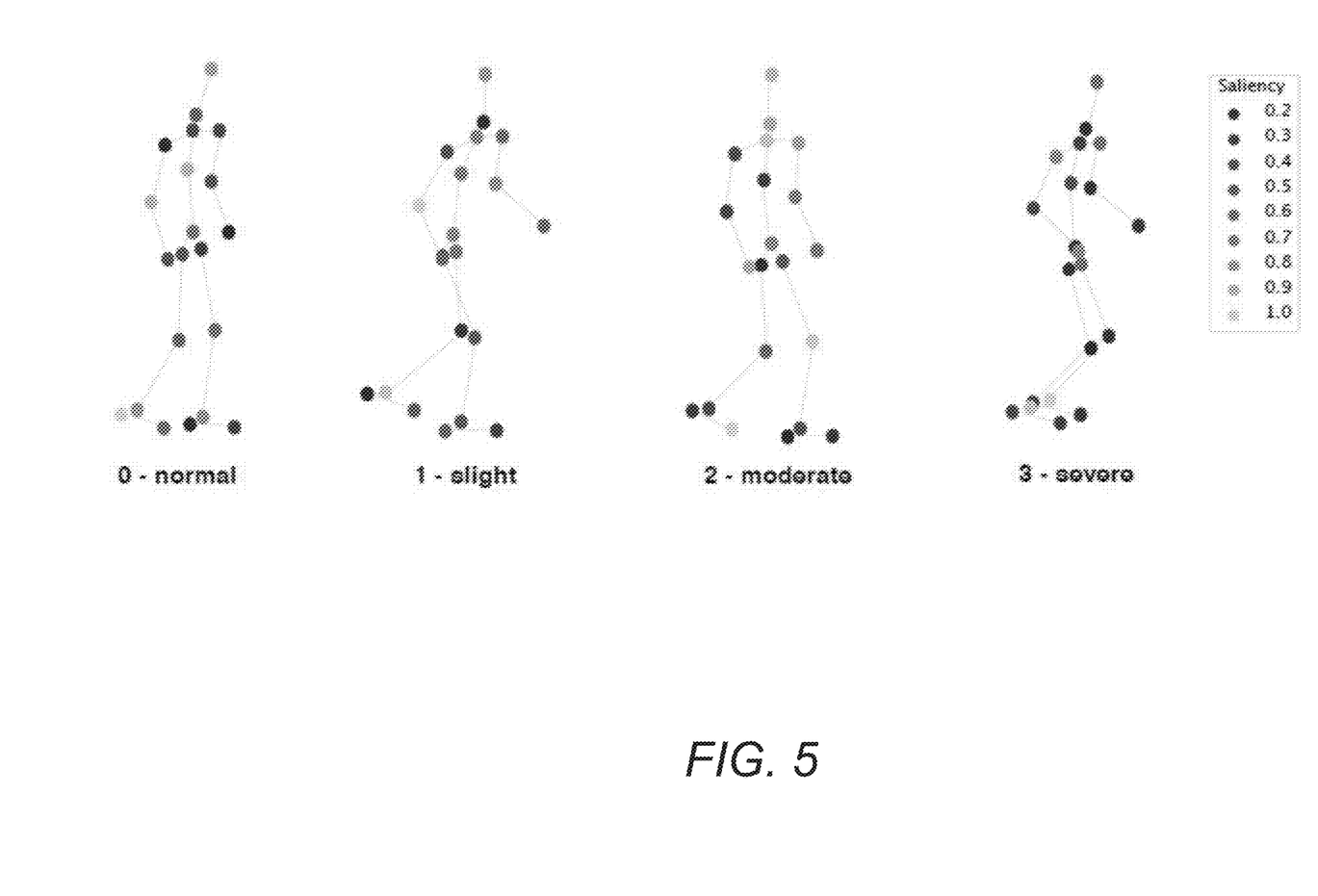
FIG. 5 illustrates saliency of 4 participants, whose gait trajectories are visualized in FIG. 1 in accordance with an embodiment of the invention.

To understand which body joints contributed the most in correctly estimating the MDS-UPDRS gait scores, many embodiments provide saliency visualizations based on the size of the gradient updates to the model. Saliency can be calculated as the average gradient update size per joint normalized to a scale from 0 to 1. FIG. 5 shows the saliency of 4 participants, whose gait trajectories are visualized in FIG. 1. Heels, ankles and toes in the feet have highest saliency, with moderate values around the arms and torso. The participant with Score 0 has highest saliency at the right heel and right arm. In the Score 1 example, the participant's feet have moderate saliency, particularly the left ankle. The arms and upper torso also represent moderate saliency, with very high saliency at the right elbow. This is corroborated by the video exam, as this patient has a stationary right arm with no bend. On the other hand, the left arm has a moderate arm swing, thus the high saliency in only the right arm matches clinical expectations. The participant with Score 2 has right toes and left knee with highest saliency. The initial clips did not have high saliency at the knee, but after the patient turned and started walking back, saliency at the left knee greatly intensified. In the score 3 sample, the model places very high saliency at both ankles. This participant's ankles do not bend at all when walking, which is one of the primary indicators of severe gait impairment and should be scored as 3.

Figure 6:
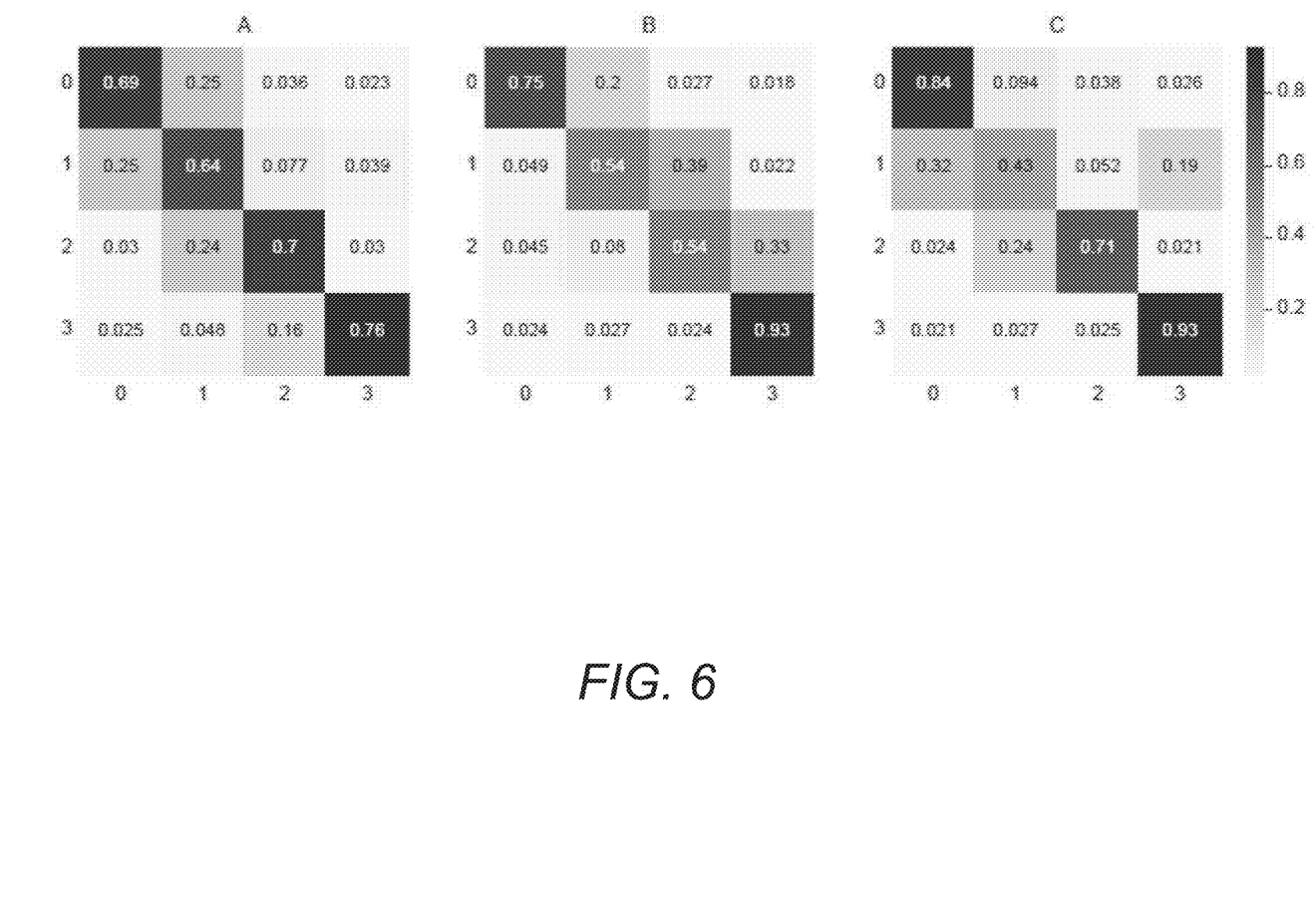
FIG. 6 illustrates learned confusion matrices of a mean CM estimates for each rater in accordance with an embodiment of the invention.

Many embodiments can additionally produce and visualize the learned confusion matrices of the mean CM estimates for each rater as illustrated in FIG. 6 in accordance with an embodiment of the invention. In particular, the confusion matrix $A^{(r)}$ for rater r is the probability that r rates the ground-truth score $y_i=c$ as $y_i^{(r)}=c'$. This probability characterizes the systematic bias of rater r. All raters have strongest confidence on the diagonal, showing a clear pattern of partial consensus with the "ground-truth" learned by the model. Rater C has the highest incidence with ground-truth for score 0 and 2, Rater A has the highest such incidence for score 1, and Rater B for score 2. This shows our raters each having highest co-incidence with ground-truth for specific classes. Rater B shows a trend of "overestimating" the gait score for 1 and 2 compared to our ground-truth, while rater C tends to "underestimate." Rater A also "underestimates" with highest confusion between classes 0 and 1. Due to the nature of our ground-truth scores representing the majority vote, we note that these characterizations are not indicative of the quality of the scores, but rather their consensus with the majority vote among our clinicians. Thus, "over" and "under" estimation represent equally valid conservative opinions which either maximize for sensitivity or specificity.

Many embodiments provide for a method to predict MDS-UPDRS gait scores even with using multiple noisy scores. Furthermore, many embodiments of the system can be used to evaluate other types of PD motor severity, such as the finger tapping test. Despite potentially high noise from inter-rater scores, many embodiments of the system can generate compelling results on the gait model by utilizing the full distribution of ratings for a dataset with multiple scores.

There can be inherent subjectivity in the MDS-UPDRS scale despite attempts to standardize the exam through objective criterion (e.g., stride amplitude/speed, heel strike, arm swing). Physicians often disagree on ambiguous cases and lean toward one score versus another based on subtle cues. Clinical context suggests the results are consistent with physician experience. As corroborated in the results of certain embodi method, OF-DDNet with RCE, the most difficult classes to categorize in clinical practice can be scores 1 and 2 since the MDS-UPDRS defines its distinction from score 1 solely by "minor" versus "substantial" gait impairment, as shown in FIG. 1. This can also be verified by a test-retest reliability analysis between A* and A (scoring and rescoring of the rater A of those participants that have scores for both ratings), which resulted in a Pearson correlation of r=0.69 and an intraclass correlation of ICC=0.60. The test-retest yielded (K=0.38, $F_1$=0.4, precision=0.52, recall=0.50). Taking either set of ratings to determine the "true" class (represented as either precision or recall) produces bAcc around only 50.0%. In comparison, many embodiments of the system strongly classified the data and are superior according to these metrics against the majority vote, showing the reliability of the estimations.

Scoring the motor MDS-UPDRS exam is known to have high inter-observer variability, which was empirically evaluated to discover average Cohen's Kappa coefficient 0.35 and an agreement of 53.4%. Many embodiments of the system can achieve a Cohen's kappa of 0.49 in comparison, much higher than between all rater pairs. Crucially, this demonstrates the systems ability to synthesize score distributions and rater confusion estimation and generalize past the noise to find the salient patterns shared by all raters. The saliency visualizations provide further evidence that the model is using valid salient features from the input keypoints to make predictions. These predictions often match the features that clinicians use to rate participants, such as a concentration of attention in the heels, ankles, and toe areas of the feet, as well as conditional consideration of arm swing, bend in the knees, and overall stiffness in the torso. For different classes and participants, the model in accordance with many embodiments was able to identify unique salient features for each class and for unique participants. Performance can improve with increased information from multiple raters. Combining all scores into a majority vote during training omits information about the distribution of ratings and thereby resulted in the lowest performance. When multiple rater information was more wholly retained in the form of soft scores, this can improve results over the aggregated labels. Further preserving multiple rater data by modeling rater confusion with dual training of the estimated score distribution and the rater confusion matrices (via RCE) can produce higher performing models. In comparison, when trained on scores from a single rater, ratings may be systematically biased due to rating habits or subjective opinion of a single rater. This may enable a model to learn the habits of a single rater very well, but risks generalizability when compared with the 'true score' across multiple raters. The level of inter-observer variability can depend significantly on factors such as the application, observer expertise, and attention. Results have suggested that when scores from multiple experts are available, methods that model observer confusion as part of the training process generally perform better than methods that aggregate the scores in a separate step prior to training. Results have also shown significant gains from using scores provided by multiple experts.

Furthermore, the effectiveness of a hybrid ordinal-focal loss on the additional finger tapping experiment for tempering the effects of a small, imbalanced dataset and leveraging the ordinal nature of the MDS-UPDRS are shown. A score of 0 can be especially difficult for a model to classify, which corroborates clinical rating in which score 0 may be frequently labeled as score 1 if there are subtle but visible disturbances. The finger tapping test demonstrates the extensibility of the system to other aspects of the MDS-UPDRS exam besides the gait test.

In many embodiments, the ML datasets can be relatively small, which carries risk of overfitting and uncertainty in the results. Many embodiments of the system can mitigate this through data augmentation techniques and using simple models (DD-Net) instead of deep or complex network architectures; and the latter with leave-one-out cross validation instead of the traditional train/validation/test split used in deep learning community. Similarly, a dataset can be still imbalanced with considerably fewer examples with score 3 of the gait experiment and scores 0 and 1 of the finger tapping experiment, which can be addressed through the custom ordinal focal loss.

Figure 7:
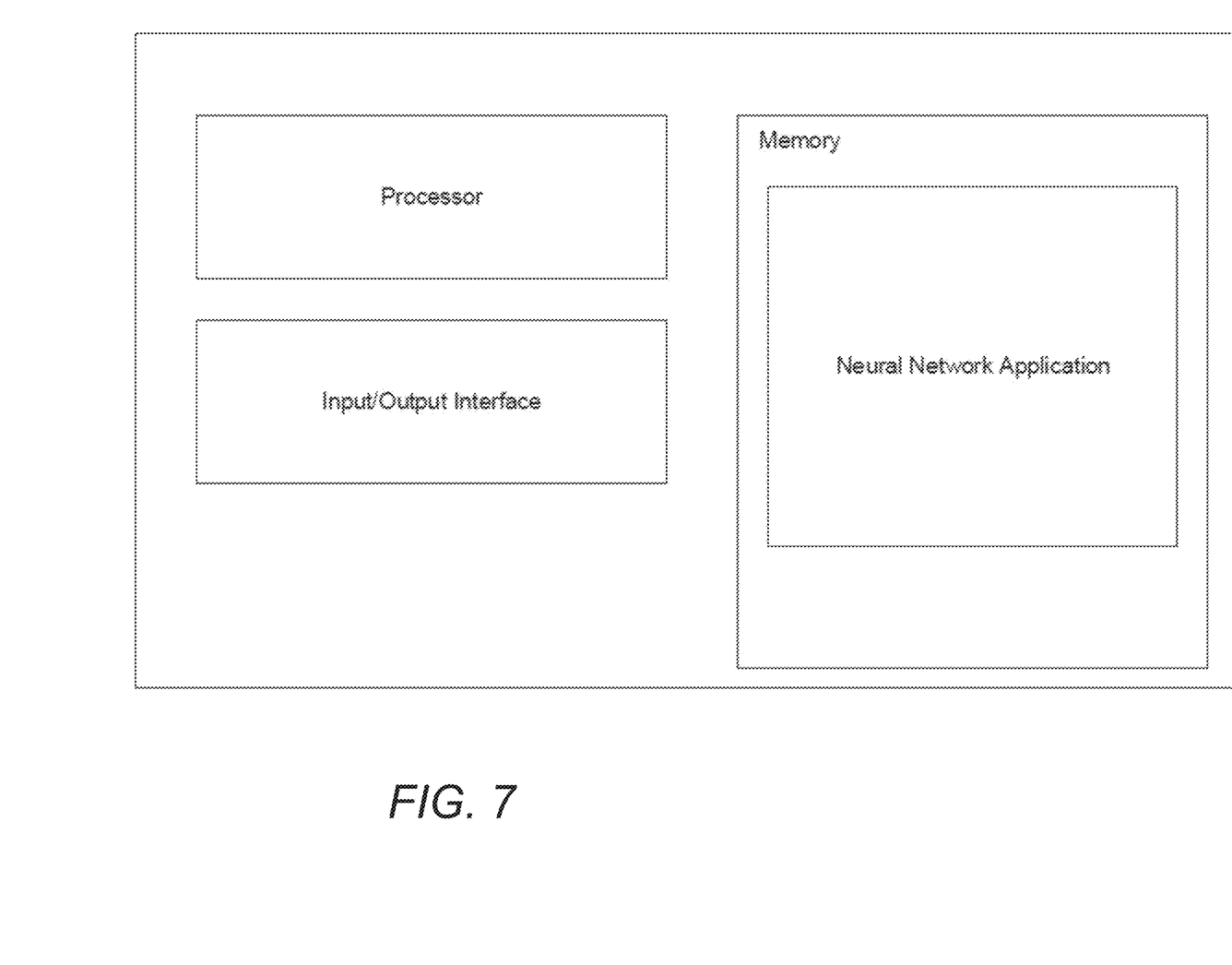
FIG. 7 illustrates a system for estimating PD using videos and machine learning that includes a processor and a memory containing an application for training a neural network in accordance with an embodiment of the invention.

In many embodiments systems and methods for estimating PD using videos and machine learning include a processor and a memory containing an application for training a neural network, as illustrated in FIG. 7.

While the above descriptions and associated figures have depicted systems and methods for estimating Parkinson's disease severity using videos and machine learning, it should be clear that any of a variety of configurations for systems and methods for estimating PD severity using videos can be implemented in accordance with embodiments of the invention. More generally, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:

1. A method for evaluating motion from a video, the method comprising:
   identifying a target individual in a set of one or more frames in a video;
   analyzing the set of frames to determine a set of pose parameters;
   generating a 3D body mesh based on the pose parameters;
   identifying joint positions for the target individual in the set of frames based on the generated 3D body mesh;
   predicting a motion evaluation score based on the identified joint positions, wherein predicting the motion evaluation score is performed using a score evaluation model that is trained using a hybrid ordinal-focal objective; and
   providing an output based on the motion evaluation score.

2. The method of claim 1, wherein identifying a target individual comprises:
   tracking a plurality of individuals in each frame of the set of frames; and
   identifying an individual that appears most often in the set of frames as the target individual.

3. The method of claim 1, wherein identifying a target individual comprises identifying a bounding box for the target individual in each of the set of frames, wherein analyzing the set of frames comprises analyzing the bounding box in each of the set of frames.

4. The method of claim 1, wherein the score evaluation model takes as input at least one of a joint collection distance (JCD) and two-scale motion features.

5. The method of claim 4, wherein the JCD and two-scale motion features are embedded into latent vectors at each frame through a series of convolutions to learn joint correlation and reduce an effect of skeleton noise.

6. The method of claim 1, wherein the motion evaluation score is a Movement Disorder Society Unified Parkinson's Disease Rating Scale (MDS-UPDRS) gait score.

7. The method of claim 1, further comprising using a trained temporal convolutional neural network (TCNN) on a sequence of 3D poses to quantify movement-linked disease markers.

8. The method of claim 7, wherein the TCNN uses a Rater Confusion Estimation (RCE) framework that jointly learns a rater scoring noise by creating a learnable confusion matrix (CM) for each rater, and wherein the method further comprises optimizing, the CM while classifying input videos using an ordinal focal strategy.

9. The method of claim 1, further comprising extracting a 2D hand skeleton of the target individual to produce a number of keypoints for the hand and using the keypoints to quantify motor impairments.

10. A system for evaluating motion from a video, the system comprising:
at least one processor; and
memory containing a motion evaluation application, wherein the motion evaluation application configures the at least one processor to:
identify a target individual in a set of one or more frames in a video;
analyze the set of frames to determine a set of pose parameters;
generate a 3D body mesh based on the pose parameters;
identify joint positions for the target individual in the set of frames based on the generated 3D body mesh;
predict a motion evaluation score based on the identified joint positions, wherein predicting the motion evaluation score is performed using a score evaluation model that is trained using a hybrid ordinal-focal objective; and
provide an output based on the motion evaluation score.

11. The system of claim 10, wherein identifying a target individual comprises:
tracking a plurality of individuals in each frame of the set of frames; and
identifying an individual that appears most often in the set of frames as the target individual.

12. The system of claim 10, wherein identifying a target individual comprises identifying a bounding box for the target individual in each of the set of frames, wherein analyzing the set of frames comprises analyzing the bounding box in each of the set of frames.

13. The system of claim 10, wherein the score evaluation model takes as input at least one of a joint collection distance (JCD) and two-scale motion features.

14. The system of claim 13, wherein the JCD and two-scale motion features are embedded into latent vectors at each frame through a series of convolutions to learn joint correlation and reduce an effect of skeleton noise.

15. The system of claim 10, wherein the motion evaluation score is a Movement Disorder Society Unified Parkinson's Disease Rating Scale (MDS-UPDRS) gait score.

16. The system of claim 10, wherein the motion evaluation application configures the at least one processor to use a trained temporal convolutional neural network (TCNN) on a sequence of 3D poses to quantify movement-linked disease markers.

17. The system of claim 16, wherein the TCNN uses a Rater Confusion Estimation (RCE) framework that jointly learns a rater scoring noise by creating a learnable confusion matrix (CM) for each rater, and wherein the the motion evaluation application further configures the at least one processor to optimize the CM while classifying input videos using an ordinal focal strategy.

18. The system of claim 10, wherein the motion evaluation application configures the at least one processor to extract a 2D hand skeleton of the target individual to produce a number of keypoints for the hand and using the keypoints to quantify motor impairments.

19. A method for evaluating motion from a video, the method comprising:
identifying a target individual in a set of one or more frames in a video;
analyzing the set of frames to determine a set of pose parameters;
generating a 3D body mesh based on the pose parameters;
identifying joint positions for the target individual in the set of frames based on the generated 3D body mesh;
using a trained temporal convolutional neural network (TCNN) on a sequence of 3D poses to quantify movement-linked disease markers;
predicting a motion evaluation score based on the identified joint positions; and
providing an output based on the motion evaluation score, wherein the TCNN uses a Rater Confusion Estimation (RCE) framework that jointly learns a rater scoring noise by creating a learnable confusion matrix (CM) for each rater; and
optimizing the CM while classifying input videos using an ordinal focal strategy.

20. The method of claim 19, further comprising extracting a 2D hand skeleton of the target individual to produce a number of keypoints for the hand and using the keypoints to quantify motor impairments.

* * * * *

UNITED STATES PATENT AND TRADEMARK OFFICE
CERTIFICATE OF CORRECTION

PATENT NO.        : 11,918,370 B2
APPLICATION NO.   : 17/324979
DATED             : March 5, 2024
INVENTOR(S)       : Ehsan Adeli-Mosabbeb et al.

Page 1 of 1

It is certified that error appears in the above-identified patent and that said Letters Patent is hereby corrected as shown below:

In the Claims

Column 12: Claim 1, Line 46 add --frames, comprising-- after "set of"; Claim 1, Line 50 add --set of-- before "pose parameters;"; Claim 2, Line 59 replace "a" with --the--; Claim 3, Line 65 replace "a" with --the--.

Column 13: Claim 10, Line 34 add --frames, comprising-- after "set of"; Claim 10, Line 38 add --set of-- before "pose parameters;"; Claim 11, Line 47 replace "a" with --the--; Claim 12, Line 53 replace "a" with --the--.

Signed and Sealed this
Sixteenth Day of December, 2025

John A. Squires
*Director of the United States Patent and Trademark Office*